United States Patent [19]

Lundquist

[11] 4,439,185
[45] Mar. 27, 1984

[54] INFLATING AND DEFLATING DEVICE FOR VASCULAR DILATING CATHETER ASSEMBLY

[75] Inventor: Ingemar H. Lundquist, Oakland, Calif.

[73] Assignee: Advanced Cardiovascular Systems, Inc., Mountain View, Calif.

[21] Appl. No.: 313,383

[22] Filed: Oct. 21, 1981

[51] Int. Cl.³ .................... A61M 29/00; A61M 25/00
[52] U.S. Cl. ........................................ 604/97; 604/99; 604/227; 604/236
[58] Field of Search ............... 128/349, 349 B, 344, 128/218 R, 218 NV, 220, 224, 234, 237, 247, 273; 604/97, 98, 100, 121, 187, 183, 218, 227, 236; 417/383, 399; 137/228, 227

[56] References Cited

U.S. PATENT DOCUMENTS

| | | | |
|---|---|---|---|
| 2,047,512 | 7/1936 | Kauffman | 604/227 |
| 2,530,909 | 11/1950 | Riggs | 128/234 X |
| 2,660,342 | 11/1953 | Ruf | 128/234 X |
| 3,952,729 | 4/1976 | Libman et al. | 128/218 NV |
| 4,015,602 | 4/1977 | Nelson et al. | 604/236 X |
| 4,082,095 | 4/1978 | Mendelson et al. | 604/236 |
| 4,271,839 | 6/1981 | Fogarty et al. | 128/349 B X |
| 4,323,071 | 4/1982 | Simpson et al. | 128/349 B X |

Primary Examiner—Stephen C. Pellegrino
Attorney, Agent, or Firm—Flehr, Hohbach, Test, Albritton & Herbert

[57] ABSTRACT

Inflating and deflating device adapted to be used by a human hand. It comprises a housing and a syringe carried by the housing. The syringe comprises a syringe body having an outlet through which liquid can pass and a piston slidably mounted in the syringe body and forming a sealing engagement with the body. A piston rod is secured to the piston and extends out of the body. A tubular member is provided. A connector means connects the tubular member to the outlet of the syringe body. A handle is carried by the housing and is secured to the syringe for causing relative movement between the piston and the syringe body. The handle means includes first and second portions movable with respect to each other. The first portion is secured to one of said piston rod or said syringe body and the other said portions are secured to one of the other of said piston rod and said syringe body. The first portion is of a size so as to be adapted to being engaged by all of the fingers of the hand and the second portion is adapted to be engaged by the palm of the hand during the time that the fingers of the hand are engaging the first portion whereby a force to cause relative movement between the piston and the syringe body can be created by that hand.

16 Claims, 7 Drawing Figures

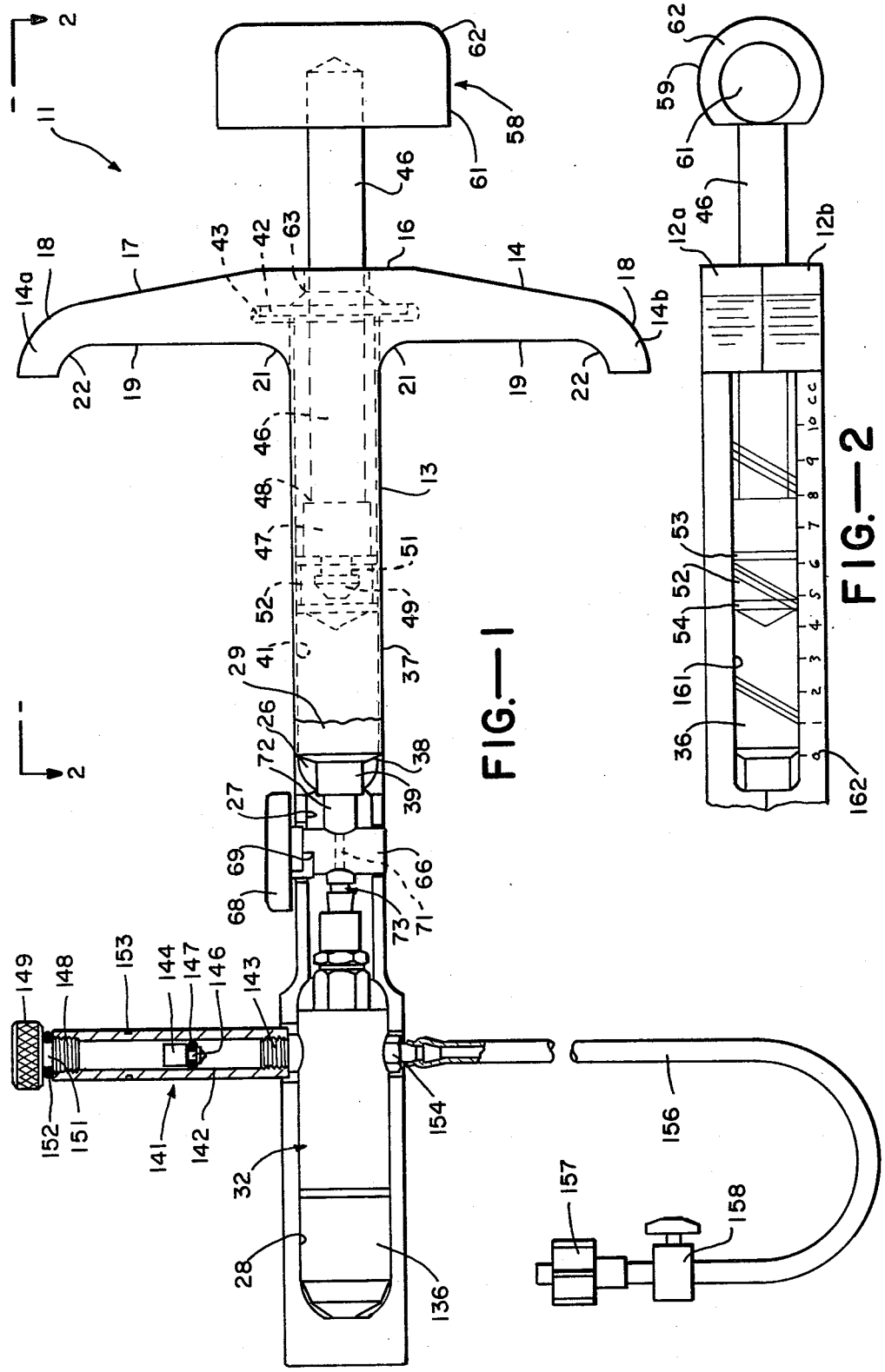

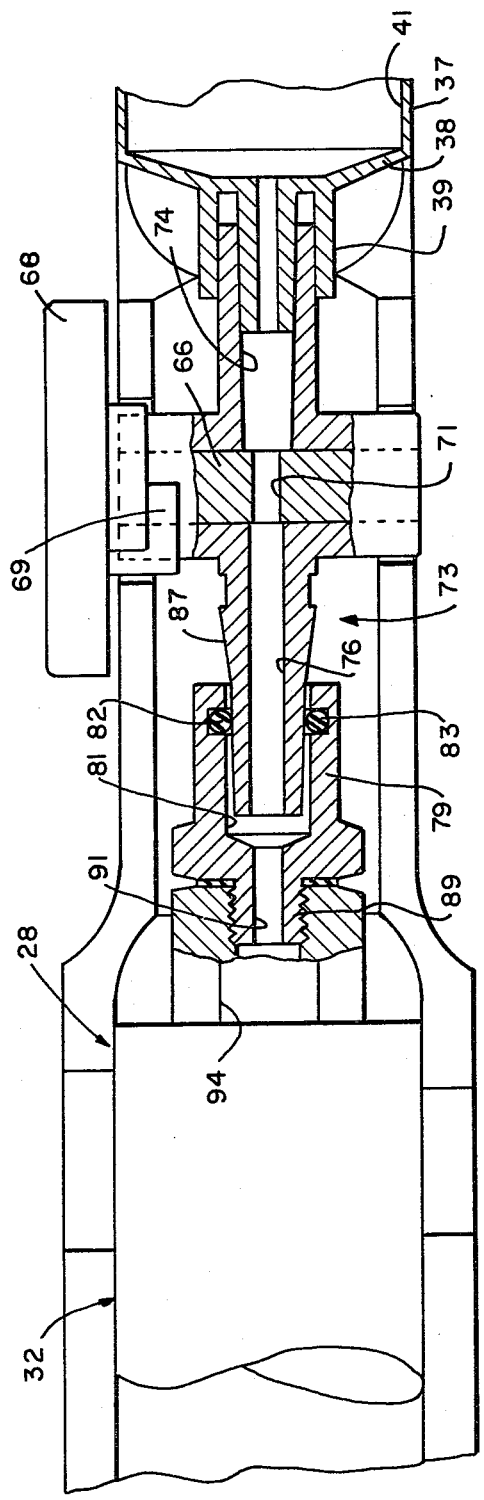
FIG.—3
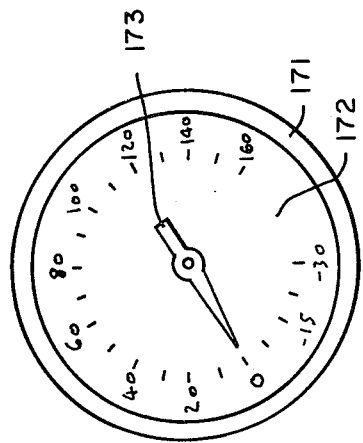
FIG.—6
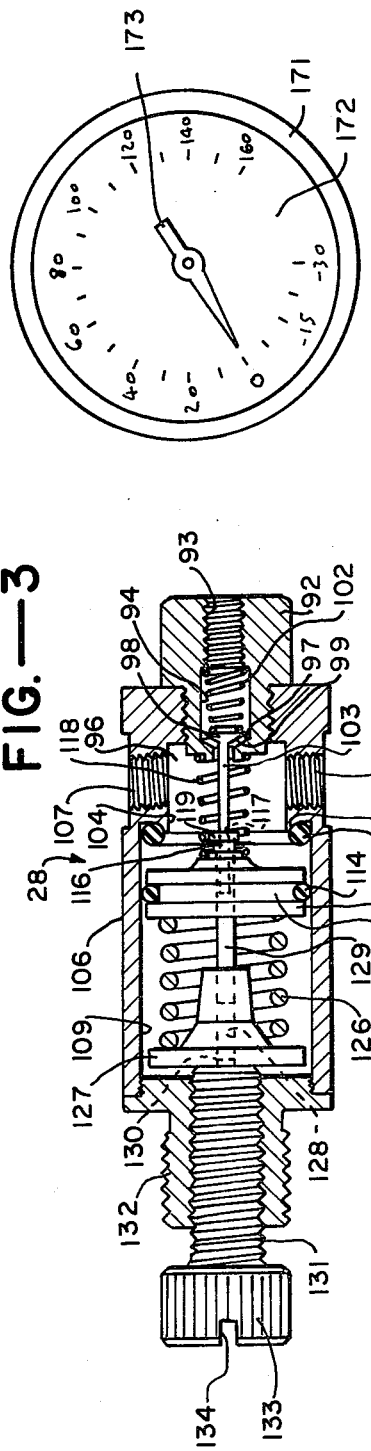
FIG.—4

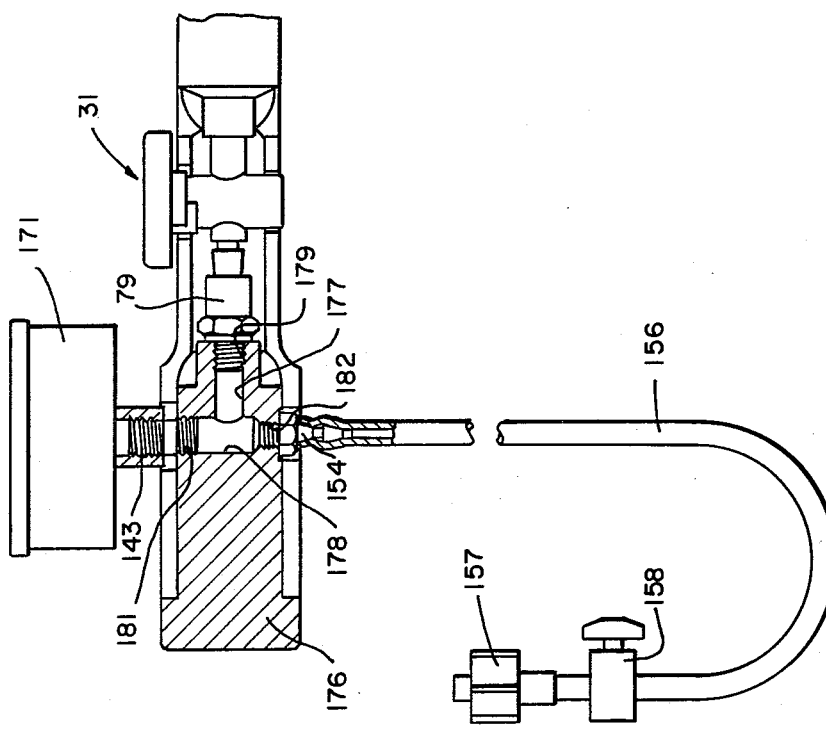
FIG.—7
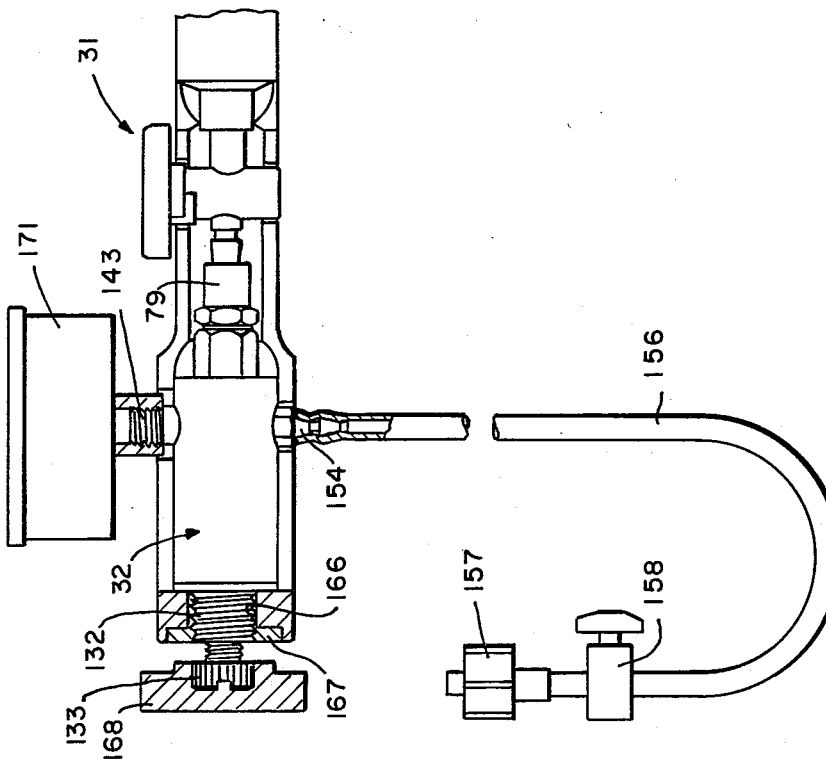
FIG.—5

INFLATING AND DEFLATING DEVICE FOR VASCULAR DILATING CATHETER ASSEMBLY

This invention relates generally to an inflating and deflating device and more particularly to an inflating and deflating device for use with a vascular dilating catheter assembly of the type which has a balloon portion near the distal end thereof which is capable of being inflated and deflated.

This application is related to application Ser. No. 06/207,732 filed on Nov. 17, 1980, now U.S. Pat. No. 4,332,254 and application Ser. No. 06/243,141 filed on Mar. 12, 1981, now abandoned.

Heretofore, vascular dilating catheter assemblies having balloons formed as a portion thereof have been inflated and deflated by the use of conventional medical-type syringes. Such a medical-type syringe has in the past been utilized with a pressure regulator and a gauge for giving an indication for the pressure being applied by the use of the syringe. In practice, it has been found that it is difficult for a doctor utilizing the medical-type syringe to apply sufficient pressure by the use of a single hand to cause inflation of the ballon. There is therefore a need for an inflating and deflating device which can be used for inflating and deflating vascular dilating catheter assemblies which overcomes the above-named disadvantages.

In general it is an object of the present invention to provide an inflating and deflating device which can be utilized for inflating and deflating vascular dilating catheter assemblies.

Another object of the invention is to provide a device of the above character in which the inflating pressure created by the device can be created by the use of a single hand of the operator.

Another object of the invention is to provide a device of the above character which has been shaped in such a manner so that it can be comfortably gripped by the hand.

Another object of the invention is to provide a device of the above character in which the pressure applied can be readily viewed from a pressure gauge carried by the device.

Another object of the invention is to provide a device of the above character in which a pressure regulator can be included in the device to predetermine the maximum pressure which can be applied for inflating a balloon.

Another object of the invention is to provide a device of the above character in which valve means is provided as a part of the device which can be operated to maintain a desired inflating pressure after it has been reached.

Another object of the invention is to provide a device of the above character in which inflating and deflating pressures obtained by the device can be maintained for a substantial period of time, time and particularly for a vacuum without leakage from the atmosphere.

Another object of the invention is to provide a device of the above character which can be readily manufactured.

Another object of the invention is to provide a device of the above character which can withstand at best a single cycle of ethylene oxide sterilization procedure.

Another object of the invention is to provide a device of the above character which is disposable after use.

Another object of the invention is to provide a device of the above character which can be readily operated by a single person.

Additional objects and features of the invention will appear from the following description in which the preferred embodiments are set forth in detail in conjunction with the accompanying drawings.

FIG. 1 is a side elevation view of an inflating and deflating device incorporating the present invention which is partly in cross-section and which utilizes a piston-type partial tubular pressure gauge.

FIG. 2 is a top plan view looking along the lines 2—2 of FIG. 1.

FIG. 3 is an enlarged cross-sectional view of a portion of the device shown in FIG. 1.

FIG. 4 is an enlarged cross-sectional view of the pressure regulator used in the embodiment of the invention shown in FIG. 1.

FIG. 5 is a partial cross-sectional view of another embodiment of the present invention utilizing a dial-type pressure gauge.

FIG. 6 is a top plan view showing the dial of the pressure gauge utilized in the embodiments of the invention shown in FIGS. 5 and 7.

FIG. 7 is a partial cross-sectional view of another embodiment of the present invention utilizing a dial-type pressure gauge, but which does not include a pressure regulator.

In general, the inflating and deflating device of the present invention which is for use with a vascular dilating catheter assembly consists of a housing. A syringe is carried by the housing and comprises a hollow syringe body having an outlet through which fluid can pass. A piston is mounted in the body and forms a sealing engagement with the body. A piston rod is secured to the piston and extends out of the end of the body remote from the outlet end. Pressure indicating means is provided. A tubular member is also provided which is adapted to be connected to the vascular dilating catheter assembly. Connecting means is provided for connecting the tubular member to the pressure indicating means and to the outlet of the syringe body. The connecting means includes valve means for interrupting the flow of fluid between the tubular member and the outlet of the syringe body.

Handle means is carried by the housing and is secured to the syringe for causing relative movement between the piston and the syringe body. The handle means includes first and second portions movable with respect to each other. The first portion is secured to one of said piston rod and said syringe body and the other said portions is secured to the other of said piston rod and said syringe body. The first portion of the handle means is adapted to be engaged by all of the fingers of the hand while the second portion is adapted to be engaged by the palm of the hand.

More particularly as shown in the drawings, the inflating and deflating device 11 of the present invention consists of a housing 12 formed in two parts or halves 12a and 12b. The housing 12 can be formed of a strong plastic such as polyvinylchloride A.S.T.M. D1784 Type I, Grade I. The housing 12 can be formed in a suitable manner such as by molding or by machining. Each of the halves 12a and 12b is provided with an eleongate body portion 13 and a handle portion 14 which is formed at one end of body portion 13 and extends generally at right angles to the longitudinal axis passing through the body portion. The handle portions 14 are solid and are provided with end portions 14a and 14b which are curved rearwardly so that the outer extremities extend generally in a direction which is parallel to the longitudinal axis of the body portion 13. Each handle portion 14 is also provided with a planar surface 16. The planar surface 16 adjoins inclined surfaces 17 which adjoin curved surfaces 18 on portions 14a and 14b. The rear side of each handle portion 14 is formed with planar surfaces 19. Curved filets 21 form a radius between the surfaces 19 and the elongate body portion 13. The surfaces 19 also adjoin curved surfaces 22 on the portions of 14a and 14b of the handle portion 14. As hereinafter described, these surfaces have been provided to facilitate a comfortable grip by all of the fingers of the hand as hereinafter described.

Each of the parts of 12a and 12b is provided with recesses 26, 27 and 28, with the recess 26 being for a syringe 29, the recess 27 for a stop cock 31 and the recess 28 for a regulator 32. The recesses 26, 27 and 28 are semi-cylindrical in shape and are of various sizes with the recess 28 being of the largest diameter, recess 26 of an intermediate diameter and the recess 27 being of the smallest diameter. All of the recesses 26, 27 and 28 are in communication with each other.

The syringe 29 which is mounted in the recess 26 is a substantially conventional medical syringe which has been modified of the type supplied by Becton-Dickinson, No. 5604 having a suitable capacity such as 10 cc. It consists of a syringe or body 36 which is formed of a suitable transparent plastic material. The syringe body 36 is provided with a cylindrical wall 37 which adjoins at one end a tapered inclined bottom wall 38. A male Luer fitting 39 is centrally disposed in the bottom wall and is in communication with a cylindrical recess 41 provided in the syringe body.

The syringe body 36 is provided with outwardly extending lips or flanges 42 which are seated in elongated recesses 43 provided in the handle portions 14 of the parts 12a and 12b. The interior cylindrical recess 41 opens through the end of the body 36 remote from the end on which the fitting 39 is mounted. A piston rod 46 formed of a suitable material such as the plastic from which the housing 12 is formed, extends through the top side of the recess 43. The rod is provided with an enlarged cylindrical portion 47 which forms a shoulder of 48. The distal end of the piston rod 46 is provided with a truncated conical tip 49. An annular recess of 51 is formed between the tip 49 and the enlarged cylindrical portion 47. A piston 52 is removably secured to the tip 49. The piston 52 is formed of suitable material such as rubber and is provided with annular spaced apart annular flanges 53 and 54 which engage the side-wall 37 of the syringe body and form a seal with respect to the sidewall 37. The piston 52 is also provided with a conical tip 56 which generally conforms to the conformation of the bottom wall 38. A handle 58 is mounted on the outer end of the piston rod 46. The handle 58 is formed in such a manner so that it represents approximately two-thirds of a cylinder. It is provided with a curved surface 59 which is adapted to be engaged by the palm of the hand. The ends of the handle 58 are provided with spaced apart planar parallel surfaces 61. Curved surfaces 62 adjoin the curved surface 59 and the planar surfaces 61.

As hereinafter described, the handle 58 is adapted to be engaged by the palm of the hand while all of the fingers of the hand can engage the handle portions 14 out of the housing 12, to the cause relative movement between the piston 52 and the syringe body 36.

A shoulder 63 is formed in handle portion 14 and is adapted to be engaged by the shoulder 44 and thus serves as a stop to prevent an operator from accidently pulling the piston 52 out of the syringe body 36.

A stop cock 31 of a conventional construction is mounted within the recess 27 and consists of body 66. The body 66 has a valve member 67 rotatably mounted therein. The valve member 67 is provided with a wing-type handle 68 which is provided for moving the valve member between open and closed positions. The body 66 is provided with shoulders 69 which serve to limit rotation of the valve member 67 for limiting the rotation of the valve member 67 between open and closed positions. The valve member 67 is provided with the flow passage 71 extending diametrically of the same which is adapted to establish communication between the inlet 72 and the outlet 73 mounted on the body 66 at diametrically opposite sides of the same. The inlet 72 is in the form of a female Luer fitting which is adapted to be connected to the male Luer fitting 39 provided on the outlet of the syringe body 36. By rotating the valve member 67 through 90 degrees, the flow passage 71 is rotated through 90 degrees so that it is out of communication with the passage of 74 provided in the inlet 72 and the passage 76 provided in the outlet 74.

The outlet 73 is tapered as shown (see FIG. 3) and is adapted to be inserted into a fitting 79. The fitting 79 is provided with a cylindrical cavity 81 which has an annular recess 82 opening into the same. An O-ring 83 is disposed in the recess 82. The O-ring 83 is adapted to receive the tapered outlet 73 of the stop cock 31 and forms a tight-sealing engagement with the tapered outlet 73.

The fitting 79 is provided with a nipple 89 which is threaded into the inlet fitting 92 of the regulator 32. The nipple 89 is provided with a flow passage 91 extending therethrough and which opens into the cavity 81. The inlet fitting 92 is provided with a threaded inlet passage 93 which opens into a cylindrical recess 94. The fitting 92 is provided with an outlet 96 which opens into the recess 94. A valve seat 97 encircles the outlet 96. A valve member 98 is provided which is movable between open and closed positions with respect to the seat 97. The valve member 98 is provided with a conical surface 99 which is adapted to engage the seat 97. It is also provided with a boss 101 which has one end of the same engaged by a spring 102. The spring 102 is disposed in the recess 94 and has its other end engaging an inner wall forming the recess 94. The valve member 98 is provided with a valve stem 103 which extends into a cylindrical recess 104 provided in a regulator body 106.

A regulator body 106 is provided and has first and second threaded outlets 107 and 108 which are in communication with the recess 104. The regulator body 106 is provided with a large cylindrical recess 109 which also opens into the recess 104. A piston assembly 111 is slidably mounted within the recess 109 for movement longitudinally thereof. It consists of a circular piston member 112 which has an annular recess 113 formed on the outer cylindrical surface thereof. An O-ring 114 is seated in the recess 113 and is adapted to form a sealing engagement with the inner wall forming the recess 109. The piston member 112 is provided with a centrally located boss 116 having a hole 117 disposed therein which is adapted to receive the valve stem 103. A coil spring 118 is disposed within the recess 104 and has one end engaging the inner extremity of the inlet fitting 92 and has the other end engaging the outer circumference of the boss 116. An annular flange or collar 119 is secured to the stem 103 and is adapted to engage the boss 116. An annular recess 121 is formed in the regulator body 106 and opens into recess 109 adjacent to recess 104 and has disposed therein an O-ring 122. The O-ring 122 is adapted to be engaged by the valve member 112 to form a fluid-tight seal. The valve member 112 is engaged by another coil spring 126 and is carried by a conically shaped boss 127 disposed within the recess 109. The boss 127 is provided with a hole 128 extending therethrough which slidably receives a piston rod 129 carried by the piston member 112. The boss 127 is rotatably mounted upon a pin 130. The pin 130 is carried by a screw 131 threaded into a fitting 132 which is threaded into the regulator body 106 to close the open end of the regulator body. A screw 131 is provided and has a knurled head 133. The head 133 is also provided with a screwdriver receiving slot 134. The screw 131 can be adjusted to provide the proper pressure from the regulator. The screw head 133 is covered with a cap 136 which is threaded onto the externally threaded fitting 132. Caps of different colors can be provided to give an indication of pressure for which the regulator has been set. For example, a cap of one color could designate a maximum 90 psi pressure whereas a cap of another color could designate a maximum pressure of 115 psi for the regulator.

Means is provided for measuring the pressure of the fluid which is created by operation of the syringe 29 and supplied through the regulator 32 consists of a piston-type pressure gauge indicator 141. Pressure gauge indicator 141 consists of a transparent plastic cylindrical member 142 which is threaded onto a nipple 143 that is threaded into the outlet 107 of the regulator 32. As can be seen, the cylindrical member 142 extends diametrically of the regulator 32. A generally cylindrical solid piston 144 is disposed within the cylindrical member 142. It is provided with an annular recess 146 adjacent to the lower extremity thereof. An O-ring 147 is seated in the recess 146 establishing a sealing engagement between the piston 144 and the inner wall of the cylindrical member 142. A screw 148 which is provided with a knurled head 149 is threaded into the upper extremity of the cylindrical member 142. The screw 148 if formed with an annular recess 151 adjacent to the head 149 which carries an O-ring 152. By loosening the screw 148, the space above the piston 144 can be vented to atmosphere by air passing between the threads. When the screw 148 is tightened, the O-ring 152 forms a seal between the screw 148 and the cylindrical member 142.

A marker indicator in the form of an annular recess 153 is provided in the outer surface of the cylindrical member 142 to indicate a predetermined pressure as for example 90 psi.

A barbed fitting 154 is mounted in the outlet 108 of the regulator 32. A flexible tubular member 156 formed of a suitable material such as plastic tubing has one end secured to the barbed fitting 154. A male Luer fitting 157 is mounted on the other end of tubular member 156. This fitting 157 is adapted to be connected to a female Luer fitting (not shown) connected to a vascular dilating catheter assembly. A conventional hose clamp or stop cock assembly 158 is mounted on the tubular member 156.

The two halves or parts 12a and 12b can be fastened together in a suitable manner. For example, when they are made of plastic as hereinbefore described, the two parts can be fastened together by ultrasonic bonding. When so bonded together they are permanently secured to each other to form a unitary housing carries the syringe 29, the stop cock 31 and the regulator 32 connected in the manner shown in FIG. 1. As can be seen from FIG. 2 when the two parts 12a and 12b have been bonded together, there are provided elongate recesses 161 on opposite sides of the housing in the vicinity of the syringe 29 so that movement of the piston 52 can be viewed through the transparent syringe body 36. As hereinbefore explained, the syringe body 36 can have a suitable size such as 10 ccs. Graduations 162 of a suitable type can be provided on the housing 12 for the syringe 29 to indicate the amount of liquid within the syringe. Thus, as shown there have been provided graduations 162 from 0 to 10 CC provided on the housing adjacent the upper recess 161.

Operation and use of the inflating and deflating device for use in inflating and deflating a vascular dilating catheter assembly can now be briefly described as follows. The device 11 is removed from its packaging which can be of a suitable type. The vent screw 148 is tightened with the piston 52 in its innermost or bottom position. To fill the syringe 29 with a radiographic contrast liquid, a needle (not shown) which is provided with a female Luer fitting is mounted on the male fitting 157. The needle can then be introduced into the rubber cap of a bottle containing the radiographic contrast liquid. This is done by pulling the piston 52 out to the location which indicates the amount of radiographic contrast liquid it is desired to draw into the syringe 29. This can be accomplished by taking the handle 14 in one hand and by grabbing the handle 58 mounted on the piston rod 46 with the other hand and withdrawing the same so as to cause relative movement between the piston 52 and the syringe body 36 to move the piston 52 to the desired position. As soon as this has been accomplished, the needle is introduced through the rubber stopper in the bottle. The device 11 is then grasped in one hand with the palm engaging the handle 58 and with all of the fingers of the hand disposed on opposite sides of the elongate body portion of 13 and engaging the surfaces 19 of the handle 14 to pressurize the bottle containing the radiographic contrast liquid. As soon as the handle 58 is released, liquid from the bottle is forced by the pressure which has been introduced in through the bottle into the tubing 156 and into the pressure regulator 32 and through the stop cock 31 and into the syringe 29. This practice is repeated until sufficient liquid has flowed from the bottle into the syringe. This procedure ensures that all air within the piston and within the passages leading to the tubular member 156 has been eliminated. By way of example the syringe 29 can be filled approximately half full, i.e., with approximately 5 ccs of radiographic contrast liquid. This normally provides enough liquid to pressurize the balloon of the vascular dilating catheter assembly and still provides enough space for vacuum action to collapse the balloon rapidly when desired.

After the device 11 has been filled with a suitable quantity of radiographic contrast liquid, the needle (not shown) is removed from the fitting 157 and the fitting 157 is connected to the vascular dilating catheter assembly which is provided with the female Luer fitting.

The balloon of the catheter assembly is filled by the doctor grasping the device in one hand with the palm again engaging the handle 58 and all of the fingers engaging the handle portion 14 and applying pressure with the hand to cause relative movement between the piston 52 and the syringe body 36. As the balloon is filled with liquid, the air in the balloon is discharged through the vent tube. When the balloon is completely filled the vent tube can be removed and the dilating catheter assembly is closed so that the balloon can be filled and collapsed by the movement of piston 52 under the control of the hand of the doctor with the palm engaging the handle 58 and the handle or handle portions 14. After it has been determined that the balloon can be readily filled with the radiographic contrast liquid and collapsed by operation of the device 11, the vascular dilating catheter assembly can be utilized in a patient in a manner well-known to those skilled in the art. The regulator 32 is set to a predetermined pressure so that no more than a predetermined pressure can be applied to the balloon. This will ensure that any pressure greater than that would rupture the balloon will not be introduced through the tubular member 156. The doctor by observing the position of the piston 144 is given a visual indication of the pressure applied to the balloon by operation of the device.

If it is desired to maintain a pre-determined pressure which has been reached, the wing-type handle 68 provided on the stop cock 31 can be rotated through 90 degrees so that the passage 71 is out of communication with the syringe 39 and the regulator 32 so that the pressure of the fluid is maintained in the tubular member 156 and in the vascular dilating catheter assembly. As soon as the stop cock 31 has been operated, the doctor can release the pressure being applied by his hand to the device 11. When it is desired to release the pressure in the balloon, it is merely necessary to again engage the handle 68 and to rotate it through 90 degrees to align the passage 71 with the regulator 32 and the syringe 29.

It has been found that the T-shaped handle 14 provided on the device makes it possible for the doctor or physician by the use of one hand to provide more than adequate pressure on the radiographic contrast liquid to inflate the vascular dilating assembly to accomplish the desired procedures with the balloon. The handle 14 is shaped in such a manner so that if desired, high pressures can be maintained by the use of one hand over a substantial period of time.

The pressure which is applied to the regulator 32 is applied to the piston member 112 and as the pressure is increased the spring 126 is depressed. As the spring is depressed, the piston moves to the left as viewed in FIG. 4, which permits the valve stem 103 to move to the left as the pressure increases. The valve stem will continue to move until the valve member 98 engages the seat 99 to prevent further flow of liquid through the regulator and therefore limits the pressure of the liquid which can be introduced into the tubular member 156. When the pressure decreases, the piston member 112 moves to the right as viewed in FIG. 4 and the boss 116 engages the collar 119 to move the valve stem 103 and the valve member 98 so that the valve member 98 clears the seat 97 to permit liquid to flow into the recess 104 to increase the pressure of the liquid in the recess 104. When the pressure in recess 104 has increased sufficiently, the piston member 112 will again move to the left as hereinbefore described so that the valve member 98 engages the seat 97.

In the event that the syringe 29 is operated to create a vacuum in the regulator 32, the piston 112 moves to the right as viewed in FIG. 6 and comes into engagement with the O-ring 122. As the vacuum is increased, greater pressure is applied to the O-ring 122 to cause it to maintain an air-tight seal between the piston and the wall forming the regulator body 106. Thus, the regulator 32 is reliable under both vacuum and pressure conditions. The O-ring 122 is seated within the recess 121 prevent the O-ring from collapsing into itself when a vacuum condition is encountered in the regulator 32.

From the foregoing it can be seen that the inflating and deflating device 11 of the present invention is particularly adapted to be held by the hand of a human being, and that it can be operated by a single hand to create a force that causes relative movement between the piston and the syringe body. Also it can be seen that connecting means is provided which includes valve means in the form of the stop cock 32. The connecting means serves to connect the tubular member 156 to the outlet of the syringe body 36 so that the pressure on the radiographic contrast liquid in the syringe body is applied to the tubular member 156. The regulator 32 is connected into the connecting means and serves to prevent a pressure greater than a predetermined pressure as determined by the adjustment on the regulator from being applied to the tubular member and to thereby prevent excessive pressures from being applied to the tubular member which could possibly burst the balloon in the vascular dilating catheter assembly. Thus, the regulator prevents pressure from being applied greater than a predetermined pressure regardless of the pressure which is created by the syringe 29.

Another embodiment of the invention is shown in FIG. 5. It is substantially identical to the embodiment of the invention shown in FIGS. 1 and 2 with the exception that the housing 12 has been shortened and has been formed with a hole 166 through which the exterior threaded extension 132 extends. A nut 167 is threaded onto the fitting 132 and engages the end of the housing 12. A knob 168 is then mounted on the head 133. The knob 168 is external to the housing 12 and can be adjusted by the physician to adjust the maximum pressure which is to be applied by the regulator 32 into the tubing 156. By making it possible to adjust for higher pressures, the physician is able to supply higher pressures to the balloon of the vascular dilating catheter assembly in order to make it possible for the physician to widen the stenosis in the artery.

In place of the piston-type pressure gauge 141, there is provided a conventional compound dial-type gauge 171 which is threaded onto the nipple 143 connected to the regulator 32. As shown in FIG. 7, the compound gauge is provided with the capability of reading pressures from 0 to 160 psi and from reading vacuums from 0 to a minus 30 psi. The gauge 171 has the advantage in that it can be set for measuring absolute pressures above a predetermined elevation as for example, sea level; whereas the gauge 141 provided in the embodiment shown in FIGS. 1 and 2 will measure the pressure above atmospheric in the location where the procedure is being performed. The gauge 171 is provided with a dial 172 on which graduations are displayed. As can be seen, the graduations are substantially linear with an equal spaces between increments. An indicator 173 is mounted on the dial for indicating the pressure which is being measured by the gauge 171. The gauge 171 has an additional advantage over the gauge 141 in that the spacing between progressive markings are substantially the same whereas on gauge 141, the spacing between the graduations become progressively smaller.

The operation of this embodiment of the invention is very similar to that hereinbefore described with the principal difference being that the physician can adjust the pressure of the liquid supplied through the tubular member 156 and can read the pressure on the dial gauge 171.

Another embodiment of the invention is shown in FIG. 7. It is similar to the embodiment shown in FIG. 5 with the exception that the regulator 32 has been omitted. In place of the regulator there has been provided a block 176 formed of a suitable material such as plastic which has been inserted into the end of the housing 12 in place of the regulator 32. It is provided with flow passages 177 and 178 which form a "T". The flow passage 177 is provided with a threaded inlet 179 into which the fitting 79 is mounted. The flow passage 178 is provided with threaded outlets 181 and 182 in which nipple 14 and the barbed fitting 154 are mounted.

The embodiment of the invention shown in FIG. 7 is similar to that hereinbefore described for the previous embodiments. The principal difference is that the regulator 32 has been omitted and the pressure which is applied to the tubular member 156 is directly under the control of the operator handling the device. The amount of pressure which is supplied is directly controlled by the amount of force which is supplied to the syringe 29 by the handle means. The doctor by watching the gauge 171 can visually observe the pressure which is being applied by the device and can thereby judge the amount of pressure which should be applied to the handle means of the device.

It is apparent from the foregoing that there has been provided a device which can be utilized for introducing radiographic contrast fluid into a vascular dilating catheter assembly and that the desired pressure of radiographic contrast liquid supplied to the balloon can be adjusted by varying the pressure applied by hand to the device. The device is particularly advantageous in that the pressure can be applied by a single hand of the operator. The "T" shaped handle is large enough so that all the fingers of the hand can be utilized for grasping the handle means. In addition, the portion which is adapted to be engaged by the palm is rounded in such a manner so that it is very comfortable to the palm of the hand. In this way, with the syringe of the type provided, pressures as high as 165 psi can be readily obtained by a mature adult human being. It should be appreciated that if higher pressures are desired, a smaller syringe could be utilized to create such pressures utilizing the same type of device. The configuration of the handle means is such that high pressure can be maintained for substantial periods of time. The device is also provided with a stop cock so that when a predetermined pressure is reached, the stop cock can be rotated to maintain this pressure permitting the operator to reduce the force being applied to the handle means of the device. The device is also fabricated in such a manner so that it can be considered to be disposable after use. It is capable of accommodating at least one ethylene oxide sterilization procedure.

What is claimed is:

1. In an inflating and deflating device adapted to be used by a human hand, a housing, a syringe carried by the housing, said syringe comprising a syringe body mounted in the housing and having an outlet through which liquid can pass, a piston slidably mounted in said body and forming a sealing engagement with the body, a piston rod secured to said piston and extending out of said body, a tubular member, connecting means carried by the housing connecting said tubular member to the outlet of said syringe body, said connecting means including valve means for controlling the flow of fluid between the outlet of the syringe body and the tubular member, pressure gauge means carried by the housing and in communication with the tubular member for measuring the pressure of the fluid in the tubular member and handle means carried by the housing and secured to said syringe for causing relative movement between the piston and the syringe body, said handle means including first and second portions movable with respect to each other, said first portion being secured to one of said piston rod and said syringe body and the other said portions being secured to the other of said piston rod and said syringe body, said first portion being of a size so as to be adapted to engaged by all of the fingers of the hand and the second portion being adapted to be engaged by the palm of the hand during the time that the fingers of the hand are engaging the first portion whereby a force to cause relative movement between the piston and the syringe body can be created by the hand.

2. A device as in claim 1 wherein said first portion of the handle means is "T" shaped.

3. A device as in claim 2 wherein said "T" shaped first portion is provided with curved outer extremities which face in a direction parallel to the longitudinal axis of the housing.

4. A device as in claim 1 wherein said second portion of the handle means is in the form of a rounded member adapted to be engaged by the palm of the hand.

5. A device as in claim 4 wherein said rounded member is generally semi-cylindrical in shape.

6. A device as in claim 1 wherein said pressure indicating means is in the form of a dial gauge.

7. A device as in claim 1 wherein said pressure indicating means is in the form of an elongate tubular member having a movable piston member therein.

8. A device as in claim 1 wherein said valve means is in the form of a stop cock having an operating handle accessible from the exterior of the housing.

9. A device as in claim 1 together with an adjustable pressure regulator connected into said connecting means for preventing the pressure of the liquid in said tubular member from exceeding a predetermined pressure as determined by adjustment of the regulator.

10. A device as in claim 9 wherein said regulator is provided with an adjustment knob which is enclosed in the housing.

11. A device as in claim 10 wherein said regulator is provided with an adjustment knob which is accessible from the housing.

12. In an inflating and deflating device adapted to be used by a human hand, a housing, a syringe carried by the housing, said syringe comprising a syringe body having an outlet through which liquid can pass, a piston slidably mounted in said body and forming a sealing engagement with the body, a piston rod secured to said piston and extending out of said body, a tubular member, connecting means connecting said tubular member to the outlet of said syringe body, handle means carried by the housing and secured to said syringe for causing relative movement between the piston and the syringe body, said connecting means including a stop cock mounted in the housing for interrupting the flow of fluid from the outlet of the syringe body to the tubular member, said handle means including first and second portions movable with respect to each other, said first portion being secured to one of said piston rod and said syringe body and the other said portions being secured to the other of said piston rod and said syringe body, said first portion being of a size so as to be adapted to be engaged by all of the fingers of the hand and the second portion being adapted to be engaged by the palm of the hand during the time that the fingers of the hand are engaging the first portion whereby a force to cause relative movement between the piston and the syringe body can be created by that hand, and regulator means connected to the connecting means for preventing a liquid pressure being applied to the tubular member greater than a predetermined pressure.

13. A device as in claim 12 together with a pressure gauge connected to the regulator for measuring the pressure of the liquid supplied to the tubular member.

14. In an inflating and deflating device adapted to be used by a human hand, a housing, a syringe carried by the housing, said syringe comprising a syringe body having an outlet through which liquid can pass, a piston slidably mounted in said body and forming a sealing engagement with the body, a piston rod secured to said piston and extending out of said body, a tubular member, connecting means connecting said tubular member to the outlet of said syringe body, handle means carried by the housing and secured to said syringe for causing relative movement between the piston and the syringe body, said handle means including first and second portions movable with respect to each other, said first portion being secured to one of said piston rod and said syringe body and the other said portions being secured the other of said piston rod and said syringe body, said first portion being of a size so as to be adapted to be engaged by all of the fingers of the hand and the second portion being adapted to be engaged by the palm of the hand during the time that the fingers of the hand are engaging the first portion whereby a force to cause relative movement between the piston and the syringe body can be created by the hand, pressure indicating means, and means connecting said pressure indicating means to said connecting means whereby said pressure indicating means measures the pressure of the liquid supplied to the tubular member, said pressure indicating means including a body having a bore therein having one end of the bore in communication with the connecting means, a piston slidably mounted in the bore, an O-ring carried by the piston and engaging the bore and screw-like means closing the other end of said bore, said screw-like means being adjustable to vent the space in the bore between the screw-like means and the piston.

15. In a disposable inflating and deflating device adapted to be used by a single human hand, a housing formed of plastic, a syringe formed of plastic and being carried by said housing, said syringe comprising a syringe body mounted in said housing, said body having a bore therein and an outlet in communication with the bore, a piston slidably mounted in the bore in said body and forming a sealing engagement with the bore, a piston rod secured to said piston and extending out of said bore in said body, a tubular member, connecting means carried by the housing connecting said tubular member to the outlet of said body of said syringe, said housing and said body of said syringe being formed in such a manner so that the piston in the bore is visible from the exterior of the body, scale means carried by the housing in juxtaposition with said piston whereby the movement of said piston can be observed with respect to said scale means and handle means carried by the housing and secured to said syringe for causing relative movement between the piston and the syringe body, said handle means including first and second portions movable with respect to each other, said first portion being secured to one of said piston rod and said syringe body and the other of said portions being secured to the other of said piston rod and said syringe body, said first portion being of size so as to be adapted to be engaged by all the fingers of the hand and the second portion being adapted to be engaged by the palm of the hand during the time that the fingers of the hand are engaging the first portion whereby a force to cause relative movement between the piston and the syringe body can be created by the single hand.

16. A device as in claim 15 wherein said connecting means includes a valve means for controlling the flow of fluid between the outlet of the syringe body and the tubular member.

* * * * *